(12) United States Patent
Trzecieski

(10) Patent No.: US 7,988,598 B2
(45) Date of Patent: Aug. 2, 2011

(54) METHOD AND APPARATUS FOR INTERFACING BETWEEN A WEARABLE ELECTRONIC DEVICE AND A SERVER AND AN ARTICLE OF FITNESS EQUIPMENT

(76) Inventor: Michael Trzecieski, Hong Kong (HK)

( * ) Notice: Subject to any disclaimer, the term of this patent is extended or adjusted under 35 U.S.C. 154(b) by 8 days.

(21) Appl. No.: 12/498,389

(22) Filed: Jul. 7, 2009

(65) Prior Publication Data
US 2010/0009810 A1    Jan. 14, 2010

Related U.S. Application Data

(60) Provisional application No. 61/078,775, filed on Jul. 8, 2008.

(51) Int. Cl.
*A63B 71/00* (2006.01)
(52) U.S. Cl. ............ 482/8; 482/1; 482/9; 482/901
(58) Field of Classification Search ............ 482/1–9, 482/900–902; 434/247
See application file for complete search history.

(56) References Cited

U.S. PATENT DOCUMENTS

| | | | | |
|---|---|---|---|---|
| 5,931,763 A * | 8/1999 | Alessandri | | 482/4 |
| 6,497,638 B1 * | 12/2002 | Shea | | 482/8 |
| 6,506,142 B2 * | 1/2003 | Itoh et al. | | 482/8 |
| 7,056,265 B1 * | 6/2006 | Shea | | 482/8 |
| 7,789,800 B1 * | 9/2010 | Watterson et al. | | 482/8 |
| 2001/0041647 A1 * | 11/2001 | Itoh et al. | | 482/9 |
| 2002/0022551 A1 * | 2/2002 | Watterson et al. | | 482/8 |
| 2004/0198555 A1 * | 10/2004 | Anderson et al. | | 482/8 |
| 2008/0090703 A1 * | 4/2008 | Rosenberg | | 482/8 |

* cited by examiner

*Primary Examiner* — Glenn Richman

(57) ABSTRACT

The user puts on a wearable electronic device at a gym and the wearable electronic device updates itself wirelessly through a server with a fitness session for the user that is stored within a plurality of user workout routines in a database as part of the server. The fitness session is a sequence of exercises the user should perform at the gym where the wearable electronic device provides an indication to the user of the various exercises. The user determines which exercises to complete and thereafter at the end of the fitness session the user's progress is stored back to the database. On a subsequent visit to the gym a second fitness session is derived based upon the first fitness session where preferably this second fitness session is derived with the assistance of a trained professional. Optionally if an article of fitness equipment is busy, the user is advised of another article of fitness equipment to utilize. Optionally the machines are equipped with a wireless interface that allows the wearable electronic device to know which machine is being used.

9 Claims, 5 Drawing Sheets

301

| Cardio | Treadmill | 30 min | — 301a |
|---|---|---|---|
| Weights | Chest Press | 6 x 120 lbs | — 301b |
| Break | | 1 min | |
| . . . | | | |
| Scale | | | — 301n |

| Cardio | Cross Trainer | 45 min | — 302a |
|---|---|---|---|
| Weights | Lat Pull down | 8 x 100 lbs | |
| Break | | 45 sec | |
| . . . | | | |
| Cardio | Treadmill | 35 min | — 302n |

METHOD AND APPARATUS FOR INTERFACING BETWEEN A WEARABLE ELECTRONIC DEVICE AND A SERVER AND AN ARTICLE OF FITNESS EQUIPMENT

CROSS REFERENCE TO RELATED APPLICATION

This application benefits from the priority of U.S. Provisional Applications 61/078,775 filed on Jul. 8, 2008, which is incorporated herein by reference.

BACKGROUND

1. Field of the Invention

The field of invention relates generally to the area of personal fitness and more specifically to data exchange between a wearable electronic device and a server for providing of a user workout routine to the wearable electronic device for directing the user in a fitness session.

2. Background Information

People are trying to get more fit these days as being fit is a sign of health. However, there are many people that are intimidated by going to the gym. Once at the gym, they typically do not know how to work out effectively and are typically inexperienced in being able to track their progress. Furthermore if they do desire to track their progress, the need to bring a notebook with them, which is cumbersome and also an additional thing that can get lost. If the person is experienced, then this notebook is typically reviewed before a future workout in order to plan the future workout. Unfortunately, the progress within the notebook is seldom reviewed by a trained professional and as such the user may be lifting too much weight or not performing enough repetitions, or they may be lifting too little weight too often. As such, the user may not obtain the progress they desire in the gym and are either wasting their time, or they are doing improper exercises and that may not be right for them and can potentially result in injury. Furthermore, they may not know what exercises they should be doing for obtaining the most benefit.

It is therefore an object of the invention to provide a method and apparatus for assisting a user in the gym that overcomes the aforementioned deficiencies.

SUMMARY OF THE INVENTION

In accordance with the invention there is provided A system for directing a user in a fitness session comprising: a wearable electronic device for being worn by the user comprising a unique identification number that is unique to the user during the fitness session and comprising a first wireless interface; a server comprising a second wireless interface for communicating with the first wireless interface of the wearable electronic device and comprising a database for storing a plurality of user workout routines where each user workout routine comprises a plurality of fitness sessions where each fitness session comprises a plurality of exercises where for the duration of a fitness session from the plurality of fitness sessions the unique identification number is correlated with the user and the fitness session, wherein for the fitness session the wearable electronic device provides an indication of at least an exercise from the plurality of exercises for the user to perform.

In accordance with the invention there is provided a method of directing a user in a fitness session comprising: providing a plurality of articles of fitness equipment; providing a server having stored therein a plurality of user workout routines where one of the plurality of user workout routines comprises a first fitness session where the first fitness session is indicative of a first sequence of articles of fitness equipment for a user to utilize from the plurality of articles of fitness equipment; providing a wearable electronic device comprising a display screen; receiving of the first fitness session by the wearable electronic device from the server; providing an indication to the user of an article of fitness equipment to utilize from the plurality of articles of fitness equipment in dependence upon the first fitness session.

In accordance with the invention there is provided a method comprising: providing a plurality of articles of fitness equipment; providing a server and a database for storing of a first fitness session; providing a wearable electronic device for being worn by a user; wireless updating of the wearable electronic device with the first fitness session comprising a plurality of exercises comprising a current exercise and a next exercise for a user to complete by using some of the plurality of articles of fitness equipment; selecting the current exercise from the plurality of exercises; providing an indication to the user of the current exercise; receiving an indication from the user upon one of completion and skipping of the current exercise; selecting the next exercise from the plurality of exercises; providing an indication to the user of the next exercise; and receiving an indication from the user upon one of completion and skipping of the next exercise.

BRIEF DESCRIPTION OF THE DRAWINGS

Exemplary embodiments of the invention will now be described in conjunction with the following drawings, in which:

FIG. 3a illustrates an exemplary first fitness session;

FIG. 3b illustrates an exemplary second fitness session;

DESCRIPTION OF EMBODIMENTS OF THE INVENTION

Figure 1A:
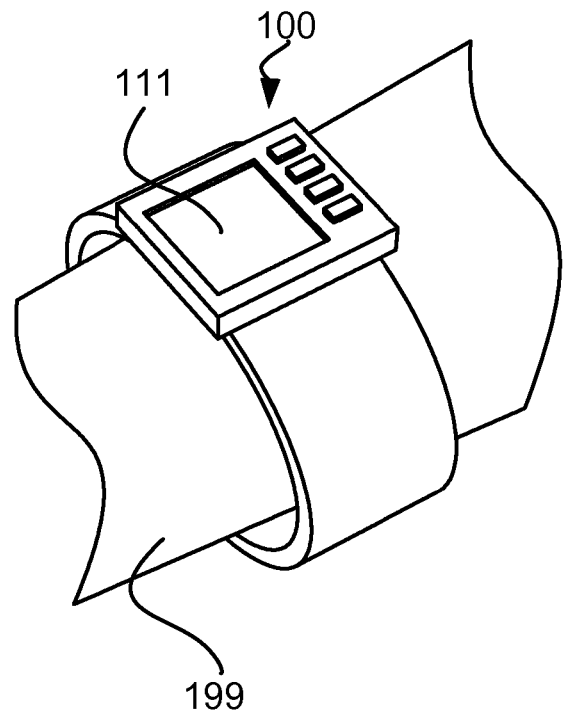
FIG. 1a illustrates a wearable electronic device in accordance with an embodiment of the invention.
Figure 1B:
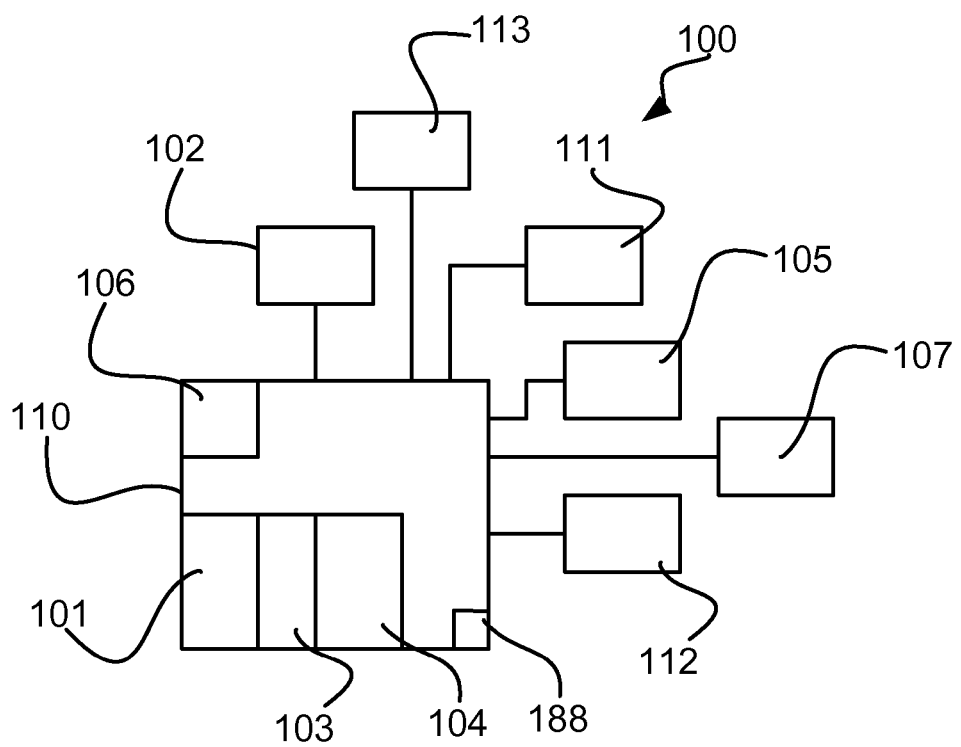
FIG. 1b illustrates components within the wearable electronic device.

FIG. 1a illustrates a wearable electronic device 100 in accordance with an embodiment of the invention. The wearable electronic device 100 is for being worn on a body part of a user 199, where this body part is preferably a wrist or hip. Referring to FIG. 1b, components within the wearable electronic device are shown, where within the wearable electronic device 100 there is disposed a control circuit 110 that is coupled with a display module 111, where the display module is optionally in the form of a touch screen display module, and a battery 112, which is preferably rechargeable. The control circuit 110 preferably includes a microcontroller 101, which is coupled with an accelerometer 102, a memory circuit 103, which is preferably FLASH memory based, a first wireless interface 104 and optionally at least a button 105. The control circuit 110 is also provided with a unique identification number 106 that is unique to the user during a fitness session. Preferably, the wearable electronic device 100 is also equipped with a vibrating motor 107. Optionally the wearable electronic device 100 includes an apparatus for heart rate monitoring 113 and further optionally the wearable electronic device comprises a heart rate interface port 188 for interfacing with a heart rate monitor.

Figure 2A:
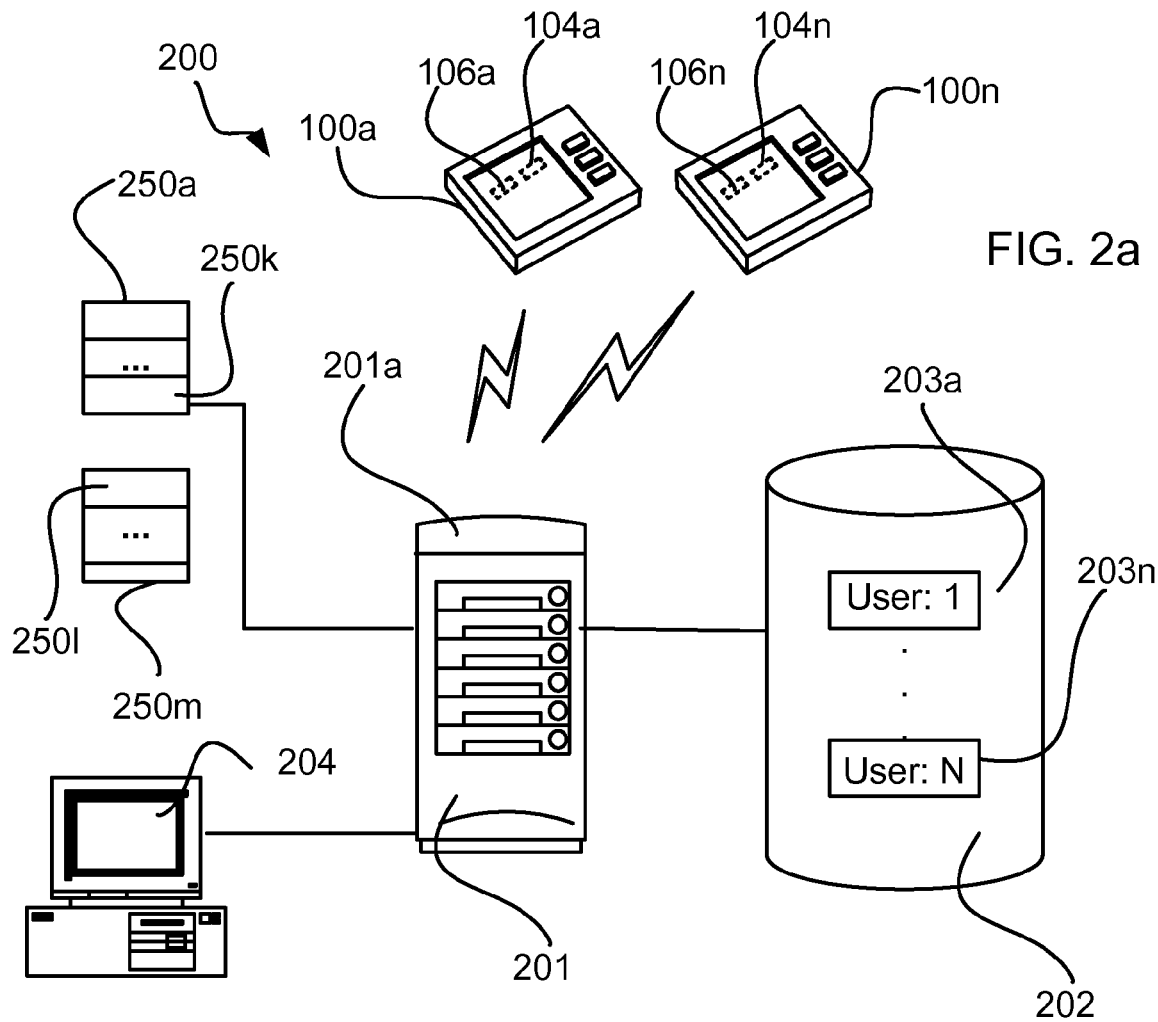
FIG. 2a illustrates a fitness session system in which the wearable electronic device operates.

FIG. 2a illustrates a fitness session system 200 in which the wearable electronic device 100 operates, where for example the fitness session system 200 is within a gym or a place of working out. Preferably the fitness session system 200 is configured to operate with a plurality of wearable electronic devices, 100a to 100n. The plurality of wearable electronic devices 100a to 100n are for communicating with a server 201, which is coupled to a database 202. Each of these wearable electronic devices is assigned the unique identification number 106a through 106n, respectively, where the database 202 is for storing of a plurality of user workout routines 203a through 203n that correspond to a plurality of users enrolled with the server 201 as part of the fitness session system 200.

Referring to FIG. 3a, a first fitness session 301 is illustrated and referring to FIG. 3b, a second fitness session 302 is illustrated. Each user workout routine, from the plurality of user workout routines 203a through 203n, comprises a plurality of fitness sessions, for example the first fitness session 301 and the second fitness session 302, where each fitness session comprises a plurality of exercises, for example 301a through 301n, where for the duration of a fitness session, 301 or 302, the unique identification number 104 is correlated with the user 199 and the fitness session, 301 or 302.

At least a computer terminal 204 is coupled with the server 201 for accessing each of the plurality of workout routines 203a through 203n stored therein. The plurality of wearable electronic devices, 100a to 100n, using the associated first wireless interface, 104a through 104n, communicate wirelessly with the server 201 using a second wireless interface 201a that is coupled with the server 201. The wearable electronic devices from the plurality of wearable electronic devices 100a through 100n are not necessarily associated with a specific user, but are correlated with the user 199 and the fitness session, 301 or 302, when the user 199 is performing of the fitness session.

For example, the user enters the gym to take part in the fitness session and when they provide their identification card, the gym in return provides the user 199 with one, 100a, of the plurality of the wearable electronic devices 100a through 100n, such that for the duration of the fitness session for the user 199, the user identification is correlated with the unique identification number, 104a, from one of the plurality of wearable electronic devices 100a through 100n as well one of the plurality of user workout routines, 203a, that are associated with that user 199.

Figure 2B:
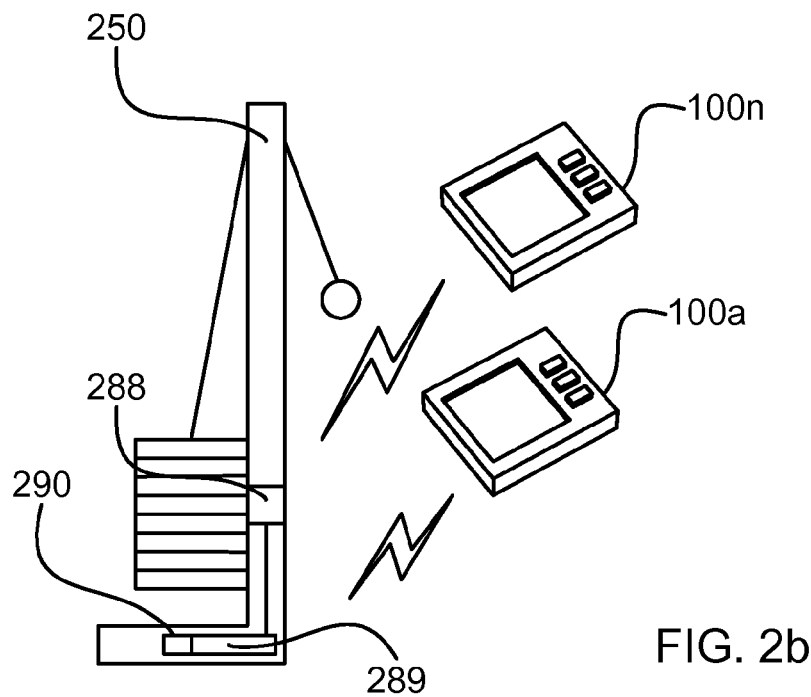
FIG. 2b illustrates an article of fitness equipment for wirelessly communicating with at least one of the plurality of wearable electronic devices.

FIG. 2b illustrates an article of fitness equipment 250 for wirelessly communicating with at least one of the plurality of wearable electronic devices, 100a to 100n, using a third wireless interface 290. The third wireless interface 290 is coupled with a control circuit 289. Preferably the control circuit 289 is coupled with an actuator 288, where the actuator 288 is used for adjusting a resistance of the article of fitness equipment 250 that is experienced by the user 199 when the user 199 interacts with the article of fitness equipment 250. For a higher resistance the user 199 experiences more weight and for lower resistance the user 199 experiences less weight.

Referring to FIG. 2a, a plurality of articles of fitness equipment, 250a through 250m are shown, where some of the plurality of articles of fitness equipment, 250a through 250k are coupled with the server 201 using either a wired or wireless coupling and the rest of the plurality of articles of fitness equipment, 250l through 250m are other than coupled with the server 200. So for example, the articles of fitness equipment 250a through 250k are workout machines, such as cardio machines, cable machines and the plurality of articles of fitness equipment, 250l through 250m are those such as free weights.

The third wireless interface 290 is preferably for determining a proximity of the wearable electronic device 100 thereto and for adjusting the resistance for the article of fitness equipment, such that when the wearable electronic device 100 is within a predetermined proximity, such as a distance of less than 50 centimeters, the actuator 288 adjusts the resistance of the article of fitness equipment 250 in dependence upon data derived from one of the plurality of fitness sessions, 301 and 302.

Referring to FIGS. 3a and 3b, the first and second fitness sessions, 301 and 302, are derived from a same user workout routine, for example 203a, from one of the plurality of user workout routines 203a through 203n. For the purposes of this disclosure, the first fitness session 301 and the second fitness session 302 are meant to be two subsequent fitness sessions, or workout sessions, and does not necessarily mean a first workout that the user has ever completed, although, it is not limited thereto. The second fitness session 302 is meant to indicate a workout sessions, or fitness session that is subsequent to the first fitness session 301.

Each fitness session, for example the first fitness session 301a, is formed from a plurality of exercises, 301a through 301n, where each exercise comprises a type of exercise, or action, an article of fitness equipment to use and duration or number of repetitions and a weight or resistance. As is shown in FIG. 3a, a first column indicates an action, a second column indicates an article of fitness equipment and a third column indicates a duration or number of repetitions and a resistance, in the form of a weight. As is shown in FIG. 3a, a first entry for the fitness session is for performing of a cardio exercise, using a treadmill, for 30 minutes. A second entry is for performing a weight exercise, using a chest press article of fitness equipment for six repetitions and a weight of 120 lbs.

Figure 4A:
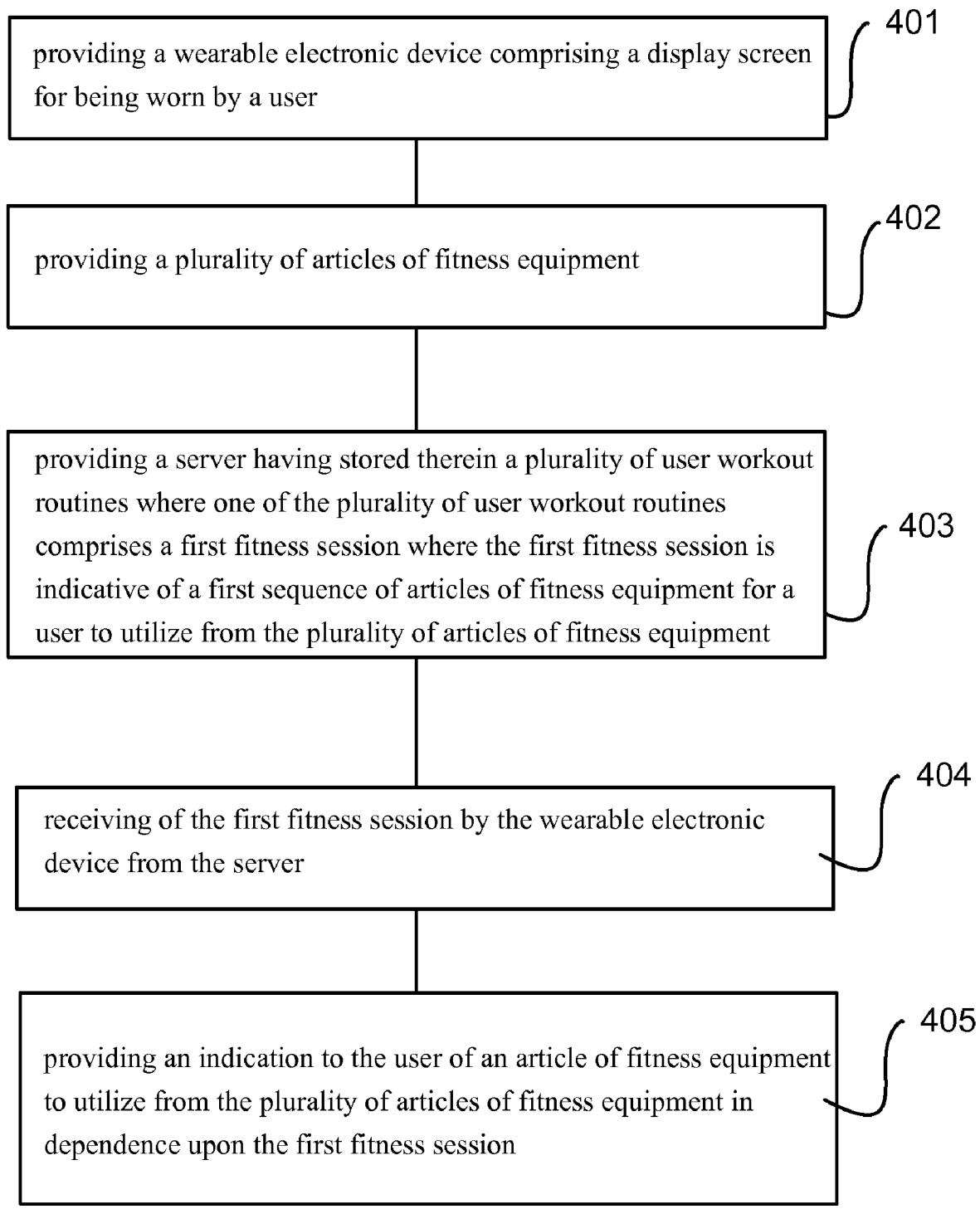
FIG. 4a illustrates a first method of operation of one of the wearable electronic devices, from the plurality of wearable electronic devices.

FIG. 4a illustrates a first method of operation of one of the wearable electronic devices 100a, from the plurality of wearable electronic devices 100a to 100n. The wearable electronic device 100a is worn by the user 199, in for example a change room of a fitness facility, such as a gym, in step 401. Within the gym or fitness facility there are provided a plurality of articles of fitness equipment, step 402. The server 201 is provided having a database 202 having stored therein a plurality of user workout routines, 203a through 203n, where one of the plurality of user workout routines, for example 203a, comprises a first fitness session, for example 301, where the first fitness session 301 is indicative of a first sequence of articles of fitness equipment in the form of a plurality of exercises, 301a through 301n, for a user 199 to utilize from the plurality of articles of fitness equipment, 250a through 250m, in step 403. As the user walks into a workout area or in a predetermined location, or locations, within the gym, the wearable electronic device 100a, receives the first fitness session 301 from the server 201, in step 404. The wearable electronic device 100a thereafter provides an indication to the user 199 of an article of fitness equipment to utilize, for example 250a, from the plurality of articles of fitness equipment 250a through 250m in dependence upon the first fitness session 301, in step 405. Preferably the indication provided to the user is a visual indication, but an audio indication is also envisaged.

As the user 199 receives the indication of the article of fitness equipment to utilize, when they are within the predetermined proximity to the article of fitness equipment to utilize, a second indication is provided. This indication is visual, an audio indication or an indication using the vibrating motor 107. Preferably, thereafter when the user 199 is within the predetermined proximity to the resistance of the article of fitness equipment from the plurality of articles of fitness equipment, the actuator 288 adjusts the resistance of the article of fitness equipment, 250*a*.

Upon the user 199 having completed utilizing at least some of first sequence of articles of fitness equipment, a second fitness session 302 is determined where the second fitness session 302 is indicative of a second sequence of articles of fitness equipment, 302*a* through 302*n* (FIG. 3*b*) for a user 199 to utilize from the plurality of articles of fitness equipment 250*a* through 250*m*, wherein the second sequence of articles of fitness equipment is derived from the first sequence of articles of fitness equipment. Preferably the second sequence of articles of fitness equipment for the user to utilize is utilized by the user on a subsequent day.

Figure 4B:
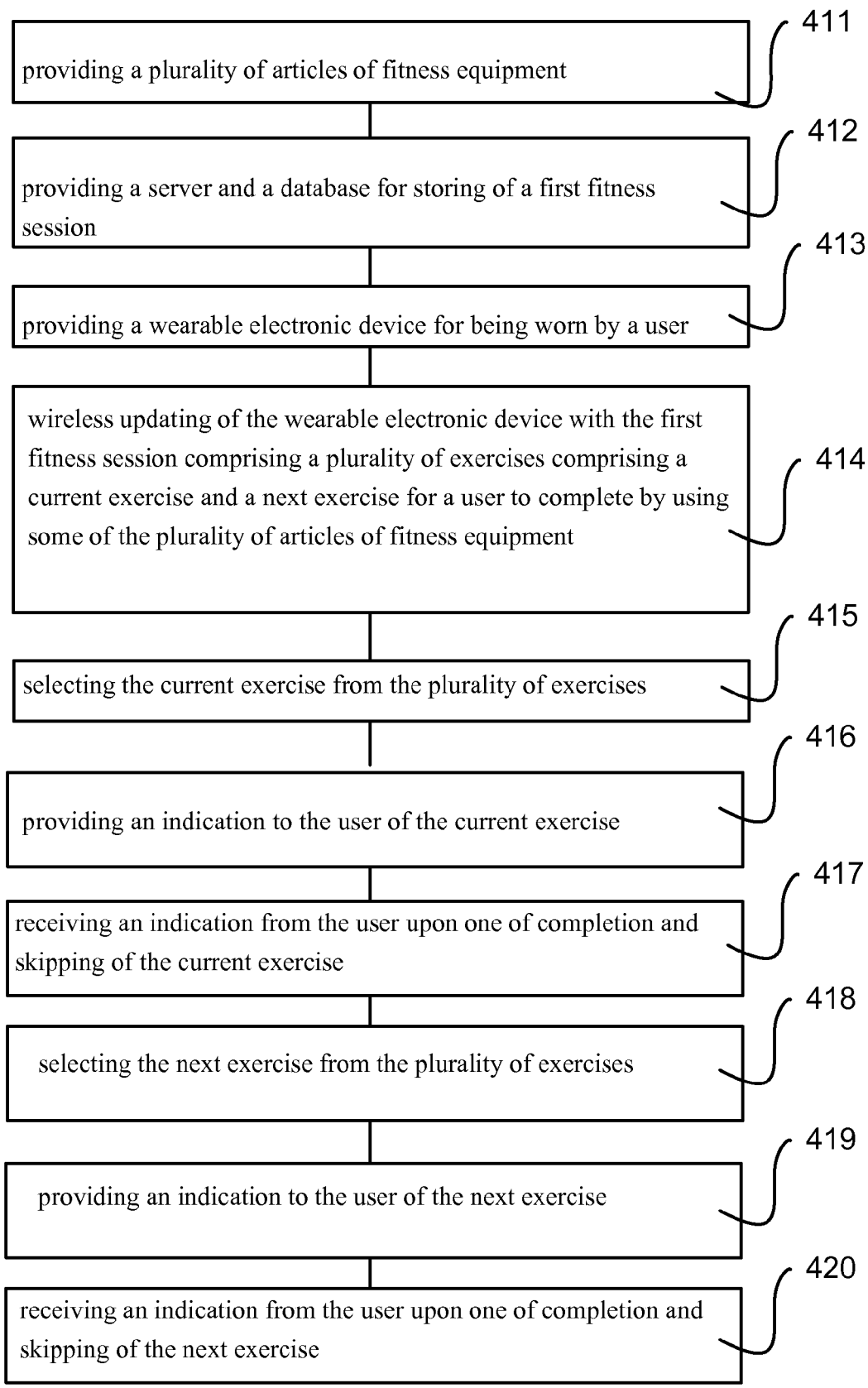
FIG. 4b illustrates a second method of operation of the wearable electronic device.

Referring to FIG. 4*b*, a second method of operation of the wearable electronic device 100*a* is shown, where in a first step 411, a plurality of articles of fitness equipment, 250*a* through 250*m* are provided. In a second step, 412, a server 201 and a database 202 for storing of the first fitness session 301 is provided. The wearable electronic device 100*a* is worn by the user 199, in step 413 and in step 414 the wearable electronic device 100*a* is updated with the first fitness session 301 comprising a plurality of exercises 301*a* through 301*n* comprising a current exercise 301*a* and a next exercise 301*b* for a user 199 to complete by using some of the plurality of articles of fitness equipment 250*a* through 250*m*. In step 415, the current exercise 301*a* is selected from the plurality of exercises 301*a* through 301*n* and in step 416 an indication is provided to the user 199 for performing of the current exercise 301*a*. The user 199 thereafter either completes the current exercise or chooses to skip the current exercise and this is received by the wearable electronic device 100*a*, in step 417. In step 418, the next exercise 301*b* from the plurality of exercises 301*a* through 301*n* is selected for the user 199 to perform and in step 419 an indication thereof is provided to the user 199. The user 199 thereafter either completes the next exercise or chooses to skip the next exercise and this is received by the wearable electronic device 100*a*, in step 420.

Upon completion of the first fitness session 301, the first fitness session as stored in the database 202 is updated in dependence upon the one of completion and skipping at least one of the current exercise 301*a* and next exercise 301*b*. Thereafter the second fitness session 302 in dependence upon the first fitness session 301 is determined for the user 199. The user 199 provides an indication to the wearable electronic device 100*a* upon them having completed the first fitness session 301.

Advantageously, if one of the article of fitness equipment from the plurality of articles of fitness equipment that is selected for the current exercise 301*a* is occupied, another article of fitness equipment from the plurality of articles of fitness equipment that is other than occupied and within the plurality of exercises is selected for the user and this minimizes waiting time that is experience by the user during their fitness session.

Referring to FIG. 1*a*, using the screen 111 of the wearable electronic device 100, or optionally through audio prompting, the user 199 is directed through at least some of the plurality of exercises that make up the fitness session, 301 or 302, by being presented a current exercise one at a time from the plurality of exercise 301*a* through 301*n*. The user attempts to perform the current exercise. Once the user 199 has preferably performed the current exercise, the user 199 pushes the at least a button 105, or optionally in the case where the screen 111 is in the form of a touch screen, to move onto the next exercise from the plurality of exercises, 301*a* through 301*n*, in the fitness session 301. Optionally, through the third wireless interface, when the used is outside the predetermined proximity of the third wireless interface, the wearable electronic device 100*a* automatically transitions to the next exercise.

Through presenting of the plurality of exercises, 301*a* through 301*n*, to the user 199, the user is directed through the fitness session 301 using the wearable electronic device 100, where the current exercise becomes the next exercise and the and the next exercise preferably becomes the subsequent exercise.

In the case where, for example, the article of fitness equipment 250, from the plurality of articles of fitness equipment, 250*a* through 250*m*, is occupied by another user or is other than useable by the user, the user 199 presses the at least a button 105 on the wearable electronic device 100 and the wearable electronic device thereafter provides an indication of another article of fitness equipment for the user to utilize from the plurality of articles of fitness equipment, 250*a* through 250*m*. Preferably the user 199 ends the fitness session 301 when they have cycled through all of the plurality of exercises, 301*a* through 301*n*. Of course, in some cases the plurality of exercises, 301*a* through 301*n*, involves the use of free weights or in a resting phase. Additionally, in the case where the plurality of articles of fitness equipment, 250*a* through 250*m*, are coupled with the server 201, the server 201 determines which articles of fitness equipment from the plurality are in use by or other than useable by the user 199 and automatically directs the user 199 to an article of fitness equipment that is available for use and that is one of the plurality exercises, 301*a* through 301*n*, for the fitness session 301.

Once at least some of the exercises from the plurality of exercises, 301*a* through 301*n*, from the first fitness session 301 have been completed by the user 199, the wearable electronic device 100 uploads progress for the first fitness session 301 to the server 201 using wireless communication between the first and second wireless interfaces, 104 and 201*a*. The progress upload occurs either automatically or by the user directing the wearable electronic device 100 to perform the upload to the server, where the upload contains data on what exercises were performed by the user during the fitness session and whether for each exercise criteria thereof were met or exceeded, such as number of repetitions. Completion of the at least some of the exercises from the plurality of exercises, 301*a* through 301*n*, for the first fitness session 301, is either provided manually by the user or automatically determined by the wearable electronic device 100.

Using the computer terminal 204, preferably a trained professional reviews the progress of the user for their performing of the first fitness session 301 as stored on the server and the trained professional updates the first fitness session 301 to form a second fitness session 302 in dependence upon a knowledge of the trained professional. On a second workout day, when the user 199 enters the gym, the wearable electronic device 100 is updated with the second fitness session 302 for the user 199. Optionally, an algorithm for execution within the server 201 generates the second fitness session from data derived from the first fitness session. In this manner, the user 199 performs a fitness session that is preferably different than a previous fitness session and as such is more beneficial to their fitness development. Having the trained professional at times monitor their progress provides an added benefit to the user 199.

Preferably, the accelerometer 102 within the wearable electronic device 100 is used to track acceleration resulting from motion of the user's arm as they perform at least some of the plurality of exercises, 301a through 301n. Preferably the accelerometer 102 is a three axis accelerometer. In addition, the accelerometer 102 preferably tracks the users pace when they are running on a treadmill or using another piece of cardio equipment that provides a measurable acceleration that has an approximate periodicity, where it functions similar to a pedometer. Software in execution within the microcontroller 101 stores date generated from the accelerometer 102 within the memory circuit 103. Preferably, for an exercise from within the plurality of exercises 301a through 301n, additional information is stored in relation to acceleration data for use by the microcontroller 101 for comparing data acquired in realtime from the accelerometer 102 to stored acceleration data. In the case where the stored acceleration data differs from the acquired in realtime data from the accelerometer, the wearable electronic device 100 triggers the motor 107 to vibrate, indicating to the user to either slow down movement of their limb or to speed up movement of their limb.

Preferably, the plurality of wearable electronic devices, 100a through 100n, are controlled in relation to each other using the server 201 such that availability for using the article of fitness equipment 250 is determined by the server 201 and the users preferably do not need to wait while the article of fitness equipment 250 is in use and are directed to another article of fitness equipment as is determined by the fitness session for each user.

Referring to FIG. 2b, preferably, the article of fitness equipment 250 is optionally electronically controllable for electronically setting a resistance thereof in the case of resistance training. In this case as the user 199 approaches the article of fitness equipment 250 and wearing the wearable electronic device 100, the article of fitness equipment 250 detects the proximity of the wearable electronic device 100 within the predetermined proximity via the third wireless interface 290, such as a RFID (radio frequency identification) interface or through RSSI (received signal strength indicator) between the first wireless interface 104 and the third wireless interface 290, and automatically adjust the resistance of the article of fitness equipment 250 using the actuator 288 in accordance with a resistance as is determined by the current exercise from the plurality of exercises, 301a through 301n, for the fitness session 301 for the user 199. This advantageously allows the user to use various articles of fitness equipment 250, from the plurality of articles of fitness equipment 250a through 250n, without having to remember the resistance as this is already predetermined for the fitness session 301.

For example, an article of fitness equipment 250 in the form of a cardio machine, such as a treadmill, has its resistance automatically adjusted based on the fitness session 301 as the user is directed by the wearable electronic device 100 to utilize the cardio machine as their current exercise. As such, the user performs their workout without having a need to remember their personal settings for the cardio machine and as they are within the predetermined proximity of the cardio machine, and preferably standing on the cardio machine, the cardio machine automatically adjust its settings in accordance with the current exercise. Optionally, the user 199 holds the wearable electronic device 100a in proximity of the third wireless interface 290 and through RFID the wearable electronic device 100a updates the cardio machine with the settings for the user 199. When the user completes using of the cardio machine, the cardio machine updates the wearable electronic device 100a with a duration that the user 199 interacted with the cardio machine.

In another example, an article of fitness equipment in the form of a shoulder press machine adjust its resistance in dependence upon a resistance specified for that article of fitness equipment as the current exercise from the plurality of exercises, 301a through 301n.

Other articles of fitness equipment, for example weighing scales, are also preferably equipped with wireless technology that facilitates communicating a weight of the user to the wearable electronic device 100 such that weight is tracked for the user by the wearable electronic device 100 and then updated on the server 201 within the database 202 within a user workout routine, from the plurality of user workout routines 203a through 203n, for the user 199.

Potentially, the wearable electronic device is in the form of an IPOD™ or an IPHONE™ that is linked with the server 201 through its wireless interface and the IPOD™ or IPHONE™ display screens are utilized for providing an indication of an exercise from the plurality of exercise for the first and second fitness sessions. Optionally the wearable electronic device comprises a MP3 player and an additional onboard memory circuit for storing of MP3 data.

In some cases the user 199 may not know how to perform the current exercise, in this case the user provides an indication to the wearable electronic device 100 that they do not know how to perform the current exercise and the wearable electronic device 100 displays an instructional video on the screen thereof in order to show the user the steps involved in performing the current exercise.

Upon a first time that a user enters the gym and they are not enrolled within the database 202, a trained professional enrolls the user and creates a user workout routine for the user 199 so that when the user thereafter is provided with the wearable electronic device 100 the wearable electronic device is updated with a fitness session.

In some cases however the article of fitness equipment is in the form of free weights, where for example coupling of barbells to the server is not feasible, in this case it is a responsibility of the user to indicate to the wearable electronic device 100 that they have met requirements associated with the current exercise when the current exercise involves free weights. A possibility however is envisaged where the free weights are also coupled with the server 201, where for example a free weight bench press machine is connected with the server and has a weight sensing device for monitoring its resistance, such that when the user is performing bench press using weights, the bench press machine communicates the resistance to the server.

Advantageously by utilizing the fitness system as described in the embodiments of the invention the users are able to track their fitness progress and potentially to improve their health in an easier manner than having to remember various exercises and weights they are to utilize for their fitness session. But utilizing the wearable electronic device they are directed through exercises for the fitness session as determined by a trained professional and they do not need to remember the weights or resistance they are to use for the various articles of fitness equipment. In addition, they are able to have their progress monitored because after they finish the first fitness session, the second fitness session is determined based on the first fitness session. It doesn't mean that always a trained professional need to update their fitness session, but it allows for a trained professional to occasionally monitor their progress and to change exercises within the fitness session to better tune progress of the user within the gym. Additionally, it also saves the user money because they to not need to train with a trained professional for every fitness session but can occasionally do so in order to ensure they are familiar with the exercises and are performing them correctly.

Numerous other embodiments may be envisaged without departing from the spirit or scope of the invention.

What is claimed is:

1. A method of directing a user in a fitness session comprising:
    providing a plurality of articles of fitness equipment;
    providing a server having stored therein a plurality of user workout routines where one of the plurality of user workout routines comprises a first fitness session where the first fitness session is indicative of a first sequence of articles of fitness equipment for a user to utilize from the plurality of articles of fitness equipment;
    providing a wearable electronic device comprising a display screen;
    receiving of the first fitness session by the wearable electronic device from the server;
    providing an indication to the user of an article of fitness equipment to utilize from the plurality of articles of fitness equipment in dependence upon the first fitness session, wherein the first fitness session comprises a plurality of exercises comprising a current exercise and a next exercise for a user to complete by using some of the plurality of articles of fitness equipment;
    selecting the current exercise from the plurality of exercises;
    providing an indication to the user of the current exercise; and
    receiving an indication from the user upon one of completion and skipping of the current exercise;
    selecting the next exercise from the plurality of exercises; and
    providing an indication to the user of the next exercise.

2. A method according to claim 1 comprising:
    determining a proximity of the wearable electronic device to the article of fitness equipment; and
    providing a second indication to the user when they are within a predetermined proximity to the article of fitness equipment to utilize from the plurality of articles of fitness equipment.

3. A method according to claim 2 comprising:
    adjusting a resistance of the article of fitness equipment to utilize from the plurality of articles of fitness equipment when the user is within the predetermined proximity.

4. A method according to claim 1 comprising:
    determining a second fitness session upon a completion of the first fitness session where the second fitness session is indicative of a second sequence of articles of fitness equipment for a user to utilize from the plurality of articles of fitness equipment, wherein the second sequence of articles of fitness equipment is derived from the first sequence of articles of fitness equipment.

5. A method comprising:
    providing a plurality of articles of fitness equipment;
    providing a server and a database for storing of a first fitness session;
    providing a wearable electronic device for being worn by a user;
    wireless updating of the wearable electronic device with the first fitness session comprising a plurality of exercises comprising a current exercise and a next exercise for a user to complete by using some of the plurality of articles of fitness equipment;
    selecting the current exercise from the plurality of exercises;
    providing an indication to the user of the current exercise;
    receiving an indication from the user upon one of completion and skipping of the current exercise;
    selecting the next exercise from the plurality of exercises;
    providing an indication to the user of the next exercise; and
    receiving an indication from the user upon one of completion and skipping of the next exercise.

6. A method according to claim 5 comprising:
    updating the first fitness session in dependence upon one of completion and skipping at least one of the current exercise and next exercise; and
    determining a second fitness session in dependence upon the first fitness session.

7. A method according to claim 6 wherein updating comprises storing of data related to the first fitness session in dependence upon one of completion and skipping at least one of the current exercise and next exercise within the database.

8. A method according to claim 5 comprising determining whether the user is aware of how to perform the current exercise and displaying an instructional video to the user in dependence upon the determination.

9. A method according to claim 5 wherein selecting the current exercise from the plurality of exercises is dependent upon determining whether an article of fitness equipment from the plurality of articles of fitness equipment that is selected for the current exercise is occupied; and
    selecting another article of fitness equipment from the plurality of articles of fitness equipment that is other than occupied and within the plurality of exercises.

* * * * *